United States Patent [19]

Vancaillie

[11] Patent Number: 5,492,537
[45] Date of Patent: Feb. 20, 1996

[54] SURGICAL FLUID MONITOR

[75] Inventor: Thierry G. Vancaillie, San Antonio, Tex.

[73] Assignee: Aquintel, Inc., Longmont, Colo.

[21] Appl. No.: 237,350

[22] Filed: May 3, 1994

[51] Int. Cl.$^6$ .................................................. A61M 5/00
[52] U.S. Cl. ........................................ 604/246; 128/760
[58] Field of Search .............................. 604/65–67, 246; 128/760; 364/413.01, 413.02

[56] References Cited

U.S. PATENT DOCUMENTS

| 4,449,538 | 5/1984 | Corbitt et al. | 128/760 |
| 4,995,268 | 2/1991 | Ash et al. | 73/861.05 |

OTHER PUBLICATIONS

W. M. Ankum, J. Vonk, "The spring balance: a simple monitoring system for fluid overload during hysteroscopic surgery," The Lancet, vol. 343, Apr. 2, 1994, pp. 836–837.

G. J. Shirk, R. J. Gimpelson, "Control of Intrauterine Fluid Pressure During Operative Hysteroscopy," The Journal of the American Association of Gynecologic Laparoscopists, vol. I, No. 3, May 1994, pp. 229–233.

Primary Examiner—Corrine M. McDermott
Attorney, Agent, or Firm—Akin, Gump, Strauss, Hauer & Feld

[57] ABSTRACT

A monitor to provide substantially real-time estimates of fluid absorbed by a patient during an endoscopic surgical procedure. The monitor weighs fluid administered to the patient intravenously, as well as that introduced through the endoscope for irrigation purposes. In addition, fluid recovered from the patient, the endoscope, the surgical drapes, and the floor is weighed. The total weight of fluid administered, reduced by automatically subtracting the total weight of fluid recovered, comprises the calculated fluid absorbed. Through manual entries and/or switch settings, totals of fluid administered and fluid collected are computed and maintained even as fluid sources are replaced and the fluid collector is emptied.

9 Claims, 5 Drawing Sheets

SURGICAL FLUID MONITOR

BACKGROUND

1. Field of the Invention

The invention relates to methods and apparatus for estimating the volume of fluid absorbed by a patient during a surgical procedure.

2. Fluid Balance in Endoscopic Surgery

Endoscopic surgery is frequently performed on the uterus (transvaginally) and the prostate gland (transurethrally). These anatomic approaches generally require that an endoscope be inserted through an orifice into a body cavity and that excised tissue be removed from the surgical site through the same orifice. To maintain the surgeon's clear view of the surgical site and facilitate continuous removal of blood and small tissue fragments, a substantially continuous flush of electrically non-conducting irrigation fluid from an external reservoir is maintained through the endoscope. Such fluid is frequently formulated as a substantially isosmotic crystalloid solution comprising one or more nonelectrolytes such as glucose, urea, glycine, mannitol, or sorbitol.

While it is intended that incidental absorption of relatively small quantities of the above irrigation fluid will not harm the patient, absorption of larger quantities may well have adverse clinical consequences. For example, if irrigation fluid under a pressure head of approximately one meter is applied to the urethra and bladder of an adult patient undergoing transurethral resection of the prostate (TURP), one may estimate that about 10 to 30 ml of irrigation fluid will be absorbed per minute of resection time. On the other hand, the absorption of as much as 6 to 8 liters of irrigation fluid has been documented during TURP's extending over a period of 2 hours. Following absorption of such large amounts of fluid, serious problems of dilutional hyponatremia and/or over-hydration may be manifest.

The latter problem can be especially serious because a patient may retain only 20% to 30% of absorbed crystalloid solution within the intravascular space. The remaining fluid generally moves to the interstitial space, where it may substantially increase the likelihood of pulmonary and cerebral edema formation. Whether or not a given patient will actually develop pulmonary and cerebral edema, however, depends on several factors, including that patient's cardiovascular status, the amount and rate of onset of the irrigation fluid load, the initial fluid volume status of the patient, and the amount of blood loss during the operation.

Thus, careful monitoring of fluid intake by the patient in real time may be very helpful when combined with other preoperative and interoperative assessments. Note that while the total fluid intake by a patient during an endoscopic surgical procedure may often be approximated by considering only the volume of irrigation fluid absorbed, fluids administered intravenously may occasionally represent a clinically significant fraction of the total fluid intake. When this occurs, accurate incorporation of intravenously administered fluids within the overall fluid balance equation is relatively easy because such fluid is usually transported directly to the vascular system with little or no loss.

In contrast, estimation of irrigation fluid absorption is error-prone because as irrigation fluid drains continuously from both the endoscope and the body orifice in which it is inserted (i.e., the vagina or urethra as the case may be), fluid is commonly distributed over the surgical drapes, operating table and floor, as well as to containers resting on the floor. Fluid falling in the containers may subsequently be manually strained to recover any tissue which is to be retained for subsequent examination. Incidental absorption by and adsorption to various operating-room surfaces, as well as losses in handling due to spillage and splashing, make irrigation fluid recovery uncertain, thereby reducing the clinical usefulness of fluid absorption estimates.

Nevertheless, because pulmonary edema formation may be life-threatening and because serious electrolyte imbalances may result in seizures, coma or death of the patient, the surgeon must have sufficient warning of impending fluid overloads and/or electrolyte imbalances to take timely corrective action. Such warning may be provided by obtaining frequent estimates of arterial oxygen tension and/or serum electrolyte levels, but obtaining this information is unduly time-consuming and inconvenient. Blood for analysis of both oxygen tension and serum electrolyte levels is usually obtained by venipuncture, leading to increased patient discomfort and increased risk to medical personnel who handle the blood samples.

A more convenient method useful for estimating a patient's overall fluid volume status during endoscopic surgery would rely on preoperative patient assessments, combined with more accurate estimates of the amount of irrigation fluid absorbed intraoperatively. For the reasons described above, however, the latter estimates are not readily available in the typical clinical setting.

SUMMARY OF THE INVENTION

The present invention answers the need for apparatus and methods to provide substantially real-time estimates of fluid absorbed by a patient during a surgical procedure. An estimate of fluid absorbed is obtained by subtracting an estimate of fluid recovered during the surgical procedure from an estimate of fluid administered during the surgical procedure, wherein the estimates are indicated by a change in a fluid collector weight and a change in a fluid source weight, respectively. Accuracy is improved through automatic fluid volume measurements and calculations, as well as by reducing the need to manually handle and/or measure waste irrigation fluid.

The invention comprises a surgical fluid monitor, the monitor in turn comprising weight-sensitive fluid support means for simultaneously suspending and weighing a fluid source. The fluid support means may comprise, for example, one or more hooks mounted on a vertical surface such as a wall, pole or equipment cart so that fluid-containing bottles, plastic bags, or similar containers may be suspended from the hook(s) to hang substantially freely, each container's weight being substantially completely supported by one hook. Fluid support means then additionally comprise a (preferably solid-state) force-sensitive device ,coupled to each hook wherein the device produces a signal indicative of the weight applied to the hook. In preferred embodiments of the invention, a solid-state load cell (i.e., a force-sensitive device comprising e.g., a piezoelectric or strain gage force sensor) is configured to allow for weighing each fluid source container supported by the fluid support means. Fluid support means thus produce a source weight signal indicative of a fluid source weight, the signal eventually being coupled to computing means by coupling means which include one or more insulated electrical conductors and/or wireless means (including a radio transmitter and receiver or, preferably, an infrared transmitter and receiver). In the latter case, the infrared transmitter for the signal indicative of a fluid source weight may preferably be battery-powered.

The surgical fluid monitor also comprises an irrigation fluid collector for collecting waste irrigation fluid. The collector preferably comprises a container having a relatively large capacity (preferably about 30 fluid liters in certain embodiments) to obviate any need for frequent emptying of the container during a surgical procedure. The container is substantially sealable and has a vacuum port (to be connected to a vacuum pump) to facilitate establishment of a partial vacuum within the container which will tend to draw irrigation fluid in through the port(s) provided in the container. Fluid collector scale means analogous to the weight-sensitive fluid support means above are coupled to the irrigation fluid collector for weighing the irrigation fluid collector and producing a collector weight signal indicative of an irrigation fluid collector weight. The collector weight signal is eventually coupled to the same computing means as the source weight signal by coupling means as described above.

The computing means is coupled to the source weight signal and the collector weight signal for calculating a fluid absorbed value, using current weights as well as prior fluid administered and prior fluid absorbed values, and for producing a display signal indicative of the calculated fluid absorbed value. The computing means is preferably a digital computer comprising a processor, a memory, a keyboard or analogous manually actuated device for entry of data and instructions, and an input-output section.

The display signal is transmitted to display means, which are thus coupled to the computing means for transducing the display signal for human observation. The display means may comprise a computer screen and/or a digital readout. In preferred embodiments, the computing means may transmit the display signal in, for example, ASCII code to a commercially available digital readout device capable of decoding and displaying ASCII-coded signals. Several such devices are available through commercial electronics parts distributors and, while not further described herein, are well-known to those skilled in the art. Note that intermediate values of variables obtained in the course of producing the calculated fluid absorbed value may also be displayed as desired.

Preferred embodiments of the surgical fluid monitor include a vacuum connection to the fluid collector container to facilitate maintenance of a partial vacuum within the container in use. The partial vacuum, in turn, facilitates entry of waste irrigation fluid into the container from sources including the endoscope drain, a drain from a floor sump or fluid-trapping floor mat, and a drain configured to recover irrigation fluid which splashes on the operating table or which emerges from a vagina or urethra (with the patient in the lithotomy position). Additionally, the fluid collector container may comprise a filter or strainer intended to separate small pieces of tissue from one or more incoming streams of waste irrigation fluid, as well as a bunghole and/or stopcock to facilitate emptying the container.

DETAILED DESCRIPTION

Figure 1:
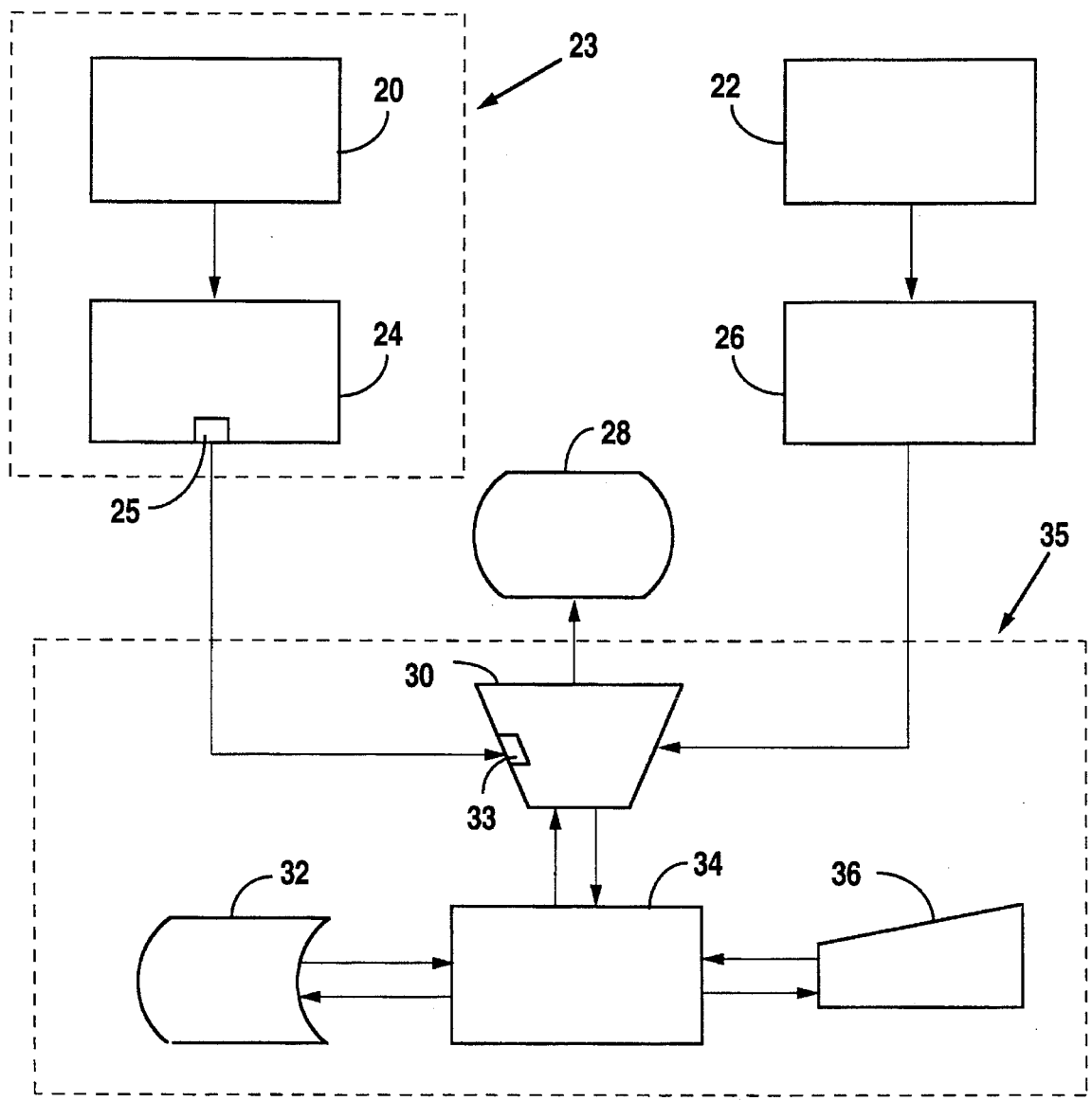
FIG. 1 schematically illustrates the flow of signals in a preferred embodiment of the invention.

Referring to FIG. 1, the signal flow in a preferred embodiment of the invention can be seen to originate in part from the weight-sensitive fluid support means 23 which comprises a fluid holder support member 20 (e.g., a hook) coupled to a weight-sensitive device 24 (e.g., a solid-state load cell). Signal flow in FIG. 1 also originates from an irrigation fluid collector 22 which in preferred embodiments is supported by fluid collector scale means 26 (e.g., a commercially available electronic scale comparable to those used for weighing patients). Signals from weight-sensitive device 24 and fluid collector scale means 26 are directed by coupling means including one or more insulated electrical conductors and/or wireless transmitter 25 (which may include, e.g., infrared transmitter 63 in FIGS. 2A,2B) to the input-output section 30 of computing means 35 (which in preferred embodiments may be configured to receive signals transmitted by insulated electrical conductor(s) and/or to receive wireless (e.g., radio or infrared) signals from wireless transmitter 25 with wireless receiver 33. Flow of signals through input-output means 30 to processor 34 and memory means 32 is controlled by processor 34 using instructions stored in memory means 32 and/or instructions from manual input device 36. Processor 34 preferably computes a calculated fluid absorbed value according to a method analogous to or substantially identical to that illustrated schematically in FIG. 4, directing the signal representing the calculated fluid absorbed value through input-output means 30 to display means 28.

Memory means 32 may comprise, for example, magnetic tape, magnetic disks, or nonmagnetic solid-state devices (e.g., optoelectronic memory or solid state switches). Manually actuated input device 36 may comprise, for example, magnetic cards, punched cards, paper or magnetic tape, a key board, or one or more switches. Processor 34 and input-output means 30 may take the form, in preferred embodiments, of the analogous sections of a personal computer, as may display means 28. However, display means 28 may comprise in addition to or in place of a computer display screen a digital readout device and/or an auditory indication of the calculated fluid absorbed value and/or auditory signals indicating when the calculated value has exceeded a limit previously stored in memory means 32 or entered into processor 34 through manual input device 36.

Figure 2A:
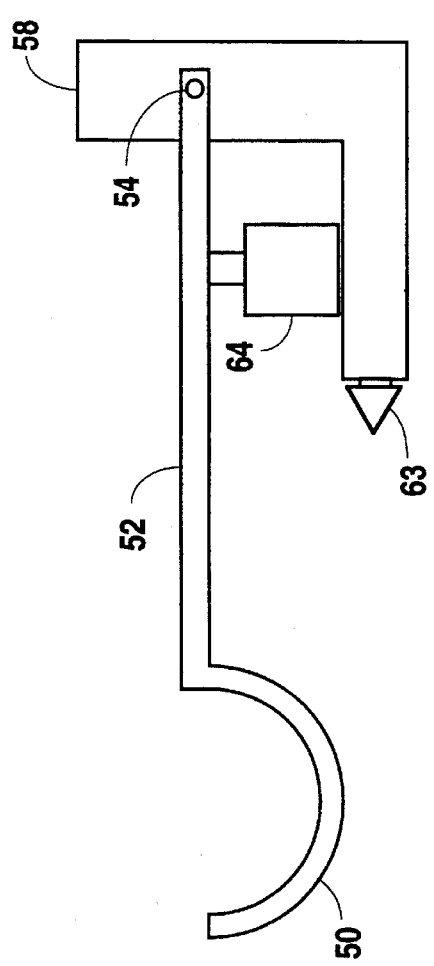
FIGS. 2A and 2B schematically illustrate alternative preferred embodiments of weight-sensitive fluid support means having a single hook to support a fluid source.
Figure 2B:
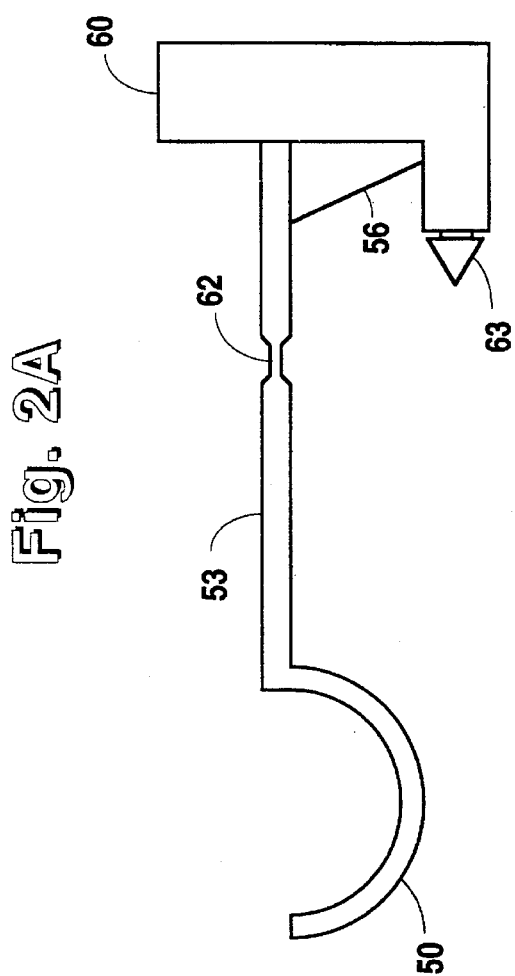

FIGS. 2A and 2B schematically illustrate examples of alternative preferred embodiments for weight-sensitive fluid supports. In FIGS. 2A and 2B, hook 50 is intended to suspend a fluid container (e.g., a plastic bag or a bottle made of glass or plastic). In FIG. 2A, hook support arm 52 is preferably substantially rigid, being pivotally coupled to support bracket 58 and being supported at an intermediate point of its length by a force-sensitive device 64 which is preferably a solid-state load cell. In FIG. 2B, hook support arm 53 is preferably substantially rigidly coupled to support bracket 60 and angle brace 56, but may deflect under load slightly due to bending which is sensed by strain gage 62. Either force-sensitive device 64 or strain gage 62 may be chosen in preferred embodiments to produce a source weight signal indicative of fluid source weight.

Support brackets 58,60 can be mounted on a wall, pole, cabinet, rack, or other suitable surface, with signals from pressure-sensitive 64 and/or strain gage 62 preferably being coupled to computing means 35 through one or more wires (not shown) or through infrared transmitter 63. In the latter case, transmitter 63 will preferably comprise a commercially available battery-powered infrared transmitter (analogous to those used to control television sets and other electrical devices) capable of transmitting an encoded version of the signals from force-sensitive device 64 and/or strain gage 62 using methods well-known to those of skill in the art. Note that weight-sensitive fluid support means may comprise one or more of the weight-sensitive fluid supports of the type schematically illustrated in FIGS. 2A, 2B. When a plurality of fluid supports is used, processor 34 is programmed to serially poll the individual fluid supports to obtain individual signals which may be combined (preferably summed) to form a signal indicative of (total) fluid source weight.

Figure 3:
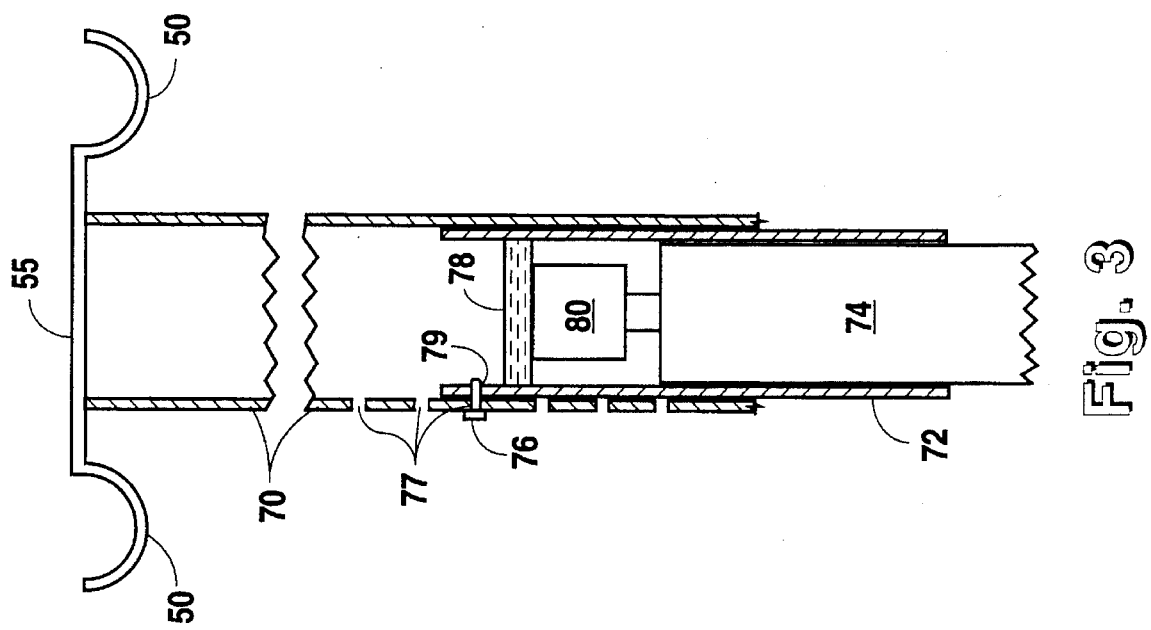
FIG. 3 schematically illustrates a partial side view (in partial cross-section) of weight-sensitive support means having a plurality of hooks to support a fluid source.

FIG. 3 schematically illustrates an alternate form of weight-sensitive fluid support means comprising a substantially cylindrical vertical support spindle 74 which fits slidingly and closely inside guide pipe 72, guide pipe 72 guiding spindle 74 to contact with compression force-sensitive member 80 (preferably a solid-state load cell) which is substantially rigidly mounted within guide pipe 72 on cross member 78. Weight applied to hooks 50 is transmitted by connector bar 55 as a substantially compressive force to outer pipe 70 and thence to guide pipe 72 through pin 76. The compressive force on guide pipe 72 is, in turn, transmitted through cross member 78 and compression force-sensitive member 80 to spindle 74 and thence through a base (shown as 94 in FIG. 5) to the earth (not shown). Note that the height of hooks 50 above base 94 (FIG. 5) can be adjusted manually through placement of pin 76 simultaneously through hole 79 in guide pipe 72 and through any one of the holes 77 in outer pipe 70.

Figure 4A:
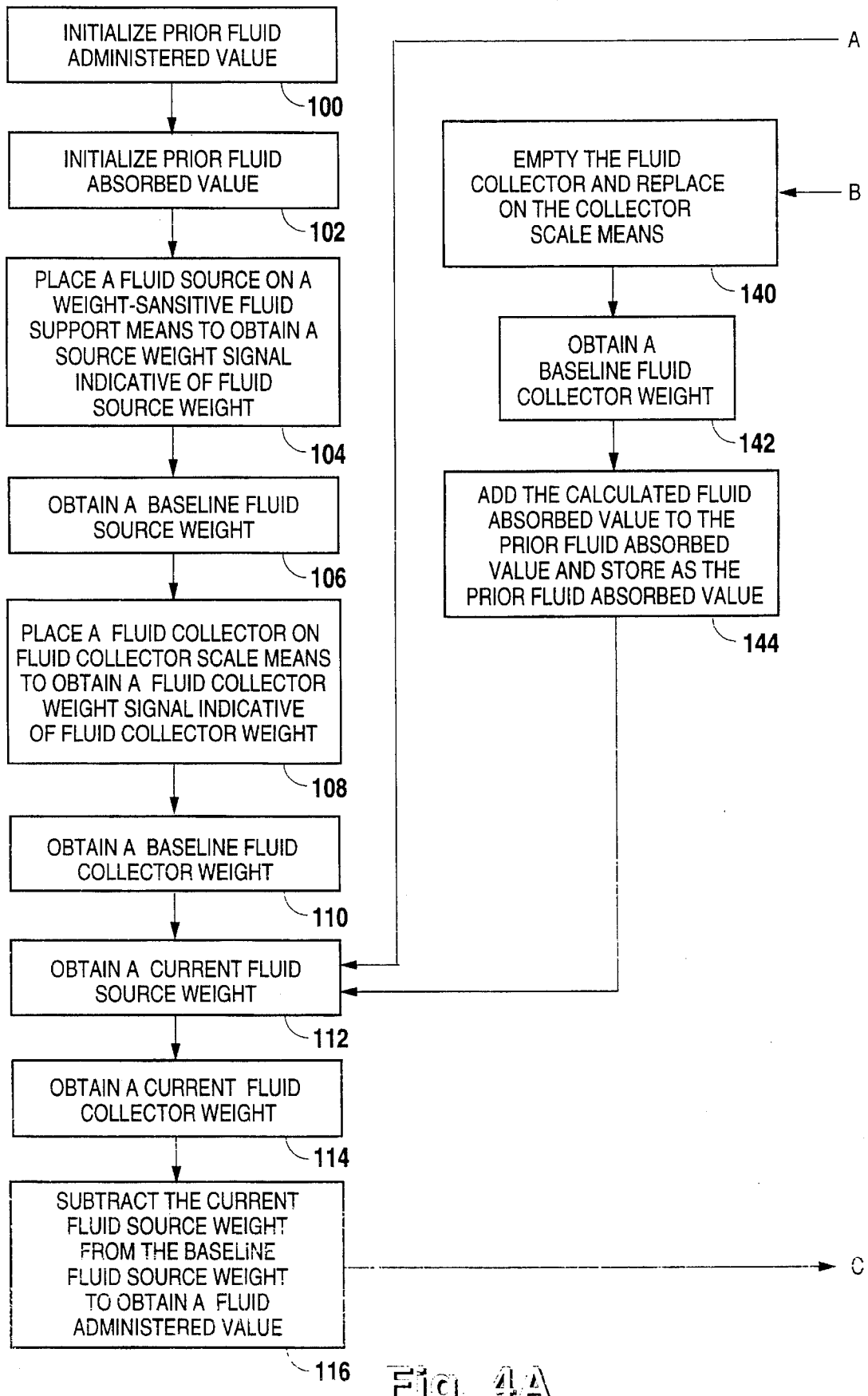
FIGS. 4A and 4B schematically illustrate details of a method for calculating a fluid absorbed value for a patient undergoing surgery.
Figure 4B:
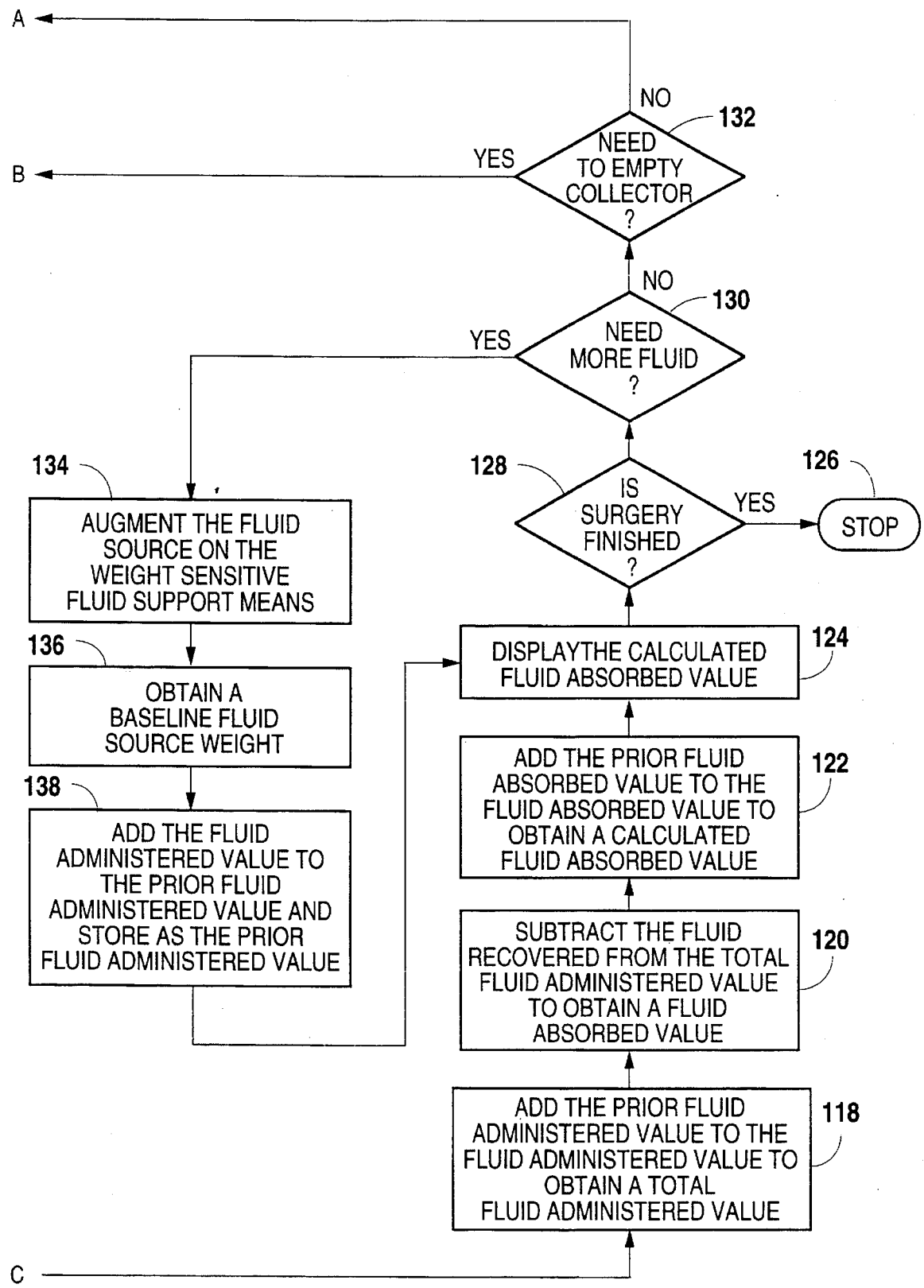

FIGS. 4A and 4B schematically illustrate a sequential series of labeled steps 100, 102, 104, 106, 108, 110, 112, 114, 116, 118, 120, 122, 124, 126, 128, 130, 132, 134, 136, 138, 140, 142 and 144 comprising a method for calculating a fluid absorbed value for a patient undergoing surgery. Note that the organization of the method steps illustrated in FIG. 4A and 4B is not unique, but is merely one embodiment of steps to accomplish the object calculation given signals indicative of fluid source weight and fluid collector weight. Specifically, one may choose in preferred embodiments of the invention to display and/or store in memory means 32 one or more of the intermediate values inherent in obtaining the object calculated value. Those skilled in the art will recognize that various steps illustrated in FIG. 4A and 4B may be interchanged and/or combined without substantially changing the method or the object calculated fluid absorbed value.

In the embodiment of FIGS. 4A and 4B, an estimate of fluid absorbed is obtained by subtracting an estimate of fluid recovered during the surgical procedure from an estimate of fluid administered during the surgical procedure, the estimates being indicated by a change in fluid collector weight and a change in fluid source weight respectively. Current weights and prior fluid administered and fluid absorbed values are used to obtain a calculated fluid absorbed value. To begin use of the embodiment of FIGS. 4A and 4B, prior fluid administered and fluid absorbed values are initialized 100,102, and a fluid source is placed on a weight-sensitive fluid support means to obtain a source weight signal indicative of fluid source weight 104. Computing means coupled to the source weight signal calculate a baseline fluid source weight 106. Analogously, a fluid collector is placed on a fluid collector scale means to obtain a fluid collector weight signal indicative of fluid collector weight 108. Computing means coupled to the collector weight signal calculate a baseline fluid collector weight 110.

At this point, a check is made to determine whether fluid should be added to the fluid source 130 and whether fluid should be emptied from the fluid collector 132. If the fluid source on the weight sensitive fluid support means is to be augmented 134, another baseline fluid source weight is obtained 136, and the fluid administered value is added to the prior fluid administered value and stored as the prior fluid administered value 138. Analogously, if the fluid collector is emptied and replaced on the collector scale means 140, another baseline fluid collector weight is obtained 142, and the calculated fluid absorbed value is added to the prior fluid absorbed value and stored as the prior fluid absorbed value 144.

The computing means then Obtains a current fluid source weight 112 and a current fluid collector weight 114. The current fluid source weight is subtracted from the baseline fluid source weight to obtain a fluid administered value 116, which is added to the prior fluid administered value to obtain a total fluid administered value 118. The fluid recovered is then subtracted from the total fluid administered value to obtain a fluid absorbed value 120, and the prior fluid absorbed value is added to the fluid absorbed value to obtain a calculated fluid absorbed value 122. The calculated fluid absorbed value is displayed 124, and it is determined whether the surgery is finished 128. If the surgery is finished, the surgical fluid monitor stops 126, but if the surgery is not finished, then it is determined whether more fluid is needed 130 and whether the collector should be emptied 132 before the above iterative process begins again.

Figure 5:
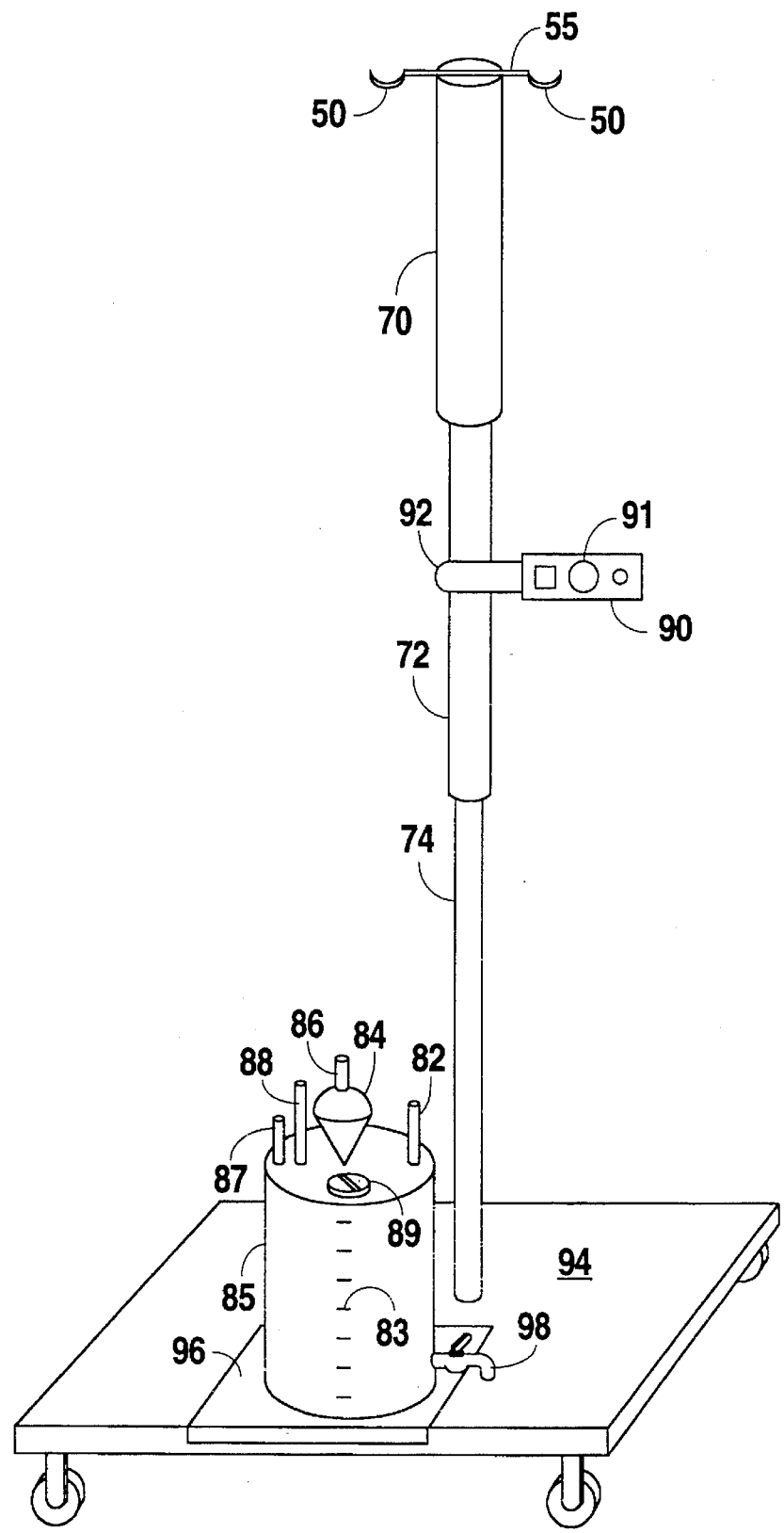
FIG. 5 schematically illustrates a preferred arrangement for weight-sensitive support means, a fluid collector and fluid collector scale means, computing means and display means.

FIG. 5 schematically illustrates one embodiment of the present invention comprising the weight-sensitive fluid support means partially illustrated in FIG. 3 in combination with a base 94, irrigation fluid collector 85, fluid collector scale means 96, and a pole-mounted embodiment 90 of computing means 35 which incorporates a digital display 91. Signals from fluid collector scale means 96 and compression force-sensitive member 80 (shown in FIG. 3) are coupled to pole-mounted embodiment 90 through one or more insulated electrical conductors (not shown) passing through pole clamp 92, leaving no exposed electrical wires to become entangled with other equipment or operating room personnel.

Irrigation fluid bags and/or intravenous fluid bags may be suspended from hooks 50 supported by connector bar 55, outer pipe 70, guide pipe 72, cross member 78, compression force-sensitive member 80, spindle 74 and base 94 as explained above. Irrigation fluid collector 85 comprises vacuum connector 82, endoscope drainage connector 86, tissue filter 84, operating table drainage connector 88 and floor sump drainage connector 87. Note that while tissue filter 84 is shown in line only with endoscope drainage connector 86, similar tissue filters 84 can also be placed in line with drainage connectors 87,88 if desired. Note also that for emptying, collector 85 may be lifted off fluid collector scale means 96 so that the contents may be poured out through bunghole 89, or the contents may alternatively be drained through stopcock 98.

What is claimed is:

1. A surgical fluid monitor, comprising weight-sensitive fluid support means for simultaneously suspending and weighing a fluid source and producing a source weight signal indicative of a fluid source weight, said fluid support means comprising at least one solid-state load cell;

an irrigation fluid collector for collecting waste irrigation fluid;

fluid collector scale means coupled to said irrigation fluid collector for weighing said irrigation fluid collector and producing a collector weight signal indicative of an irrigation fluid collector weight;

computing means coupled to said source weight signal and said collector weight signal for calculating a fluid absorbed value, and for producing a display signal indicative of a calculated fluid absorbed value;

coupling means for coupling said computing means to said source weight signal and said collector weight signal; and display means coupled to said computing means for transducing for human observation a display signal indicative of a calculated fluid absorbed value.

2. The surgical fluid monitor of claim 1 wherein said irrigation fluid collector comprises a vacuum port, an endoscope drainage port, a floor drainage port, and an operating table drainage port.

3. The surgical fluid monitor of claim 1 wherein said irrigation fluid collector comprises a screen to separate tissue pieces from irrigation fluid drainage.

4. The surgical fluid monitor of claim 1 wherein said display means comprises a digital readout.

5. The surgical fluid monitor of claim 1 wherein said display means comprises a computer monitor screen.

6. The surgical fluid monitor of claim 1 wherein said coupling means comprises wireless means.

7. The surgical fluid monitor of claim 6 wherein said wireless means comprises a radio transmitter and receiver.

8. The surgical fluid monitor of claim 6 wherein said wireless means comprises an infrared transmitter and receiver.

9. The surgical fluid monitor of claim 8 wherein said wireless transmitter is battery-powered.

* * * * *